United States Patent
Toth et al.

(10) Patent No.: US 6,370,218 B1
(45) Date of Patent: Apr. 9, 2002

(54) METHODS AND SYSTEMS FOR DETERMINING X-RAY BEAM POSITION IN MULTI-SLICE COMPUTED TOMOGRAPHY SCANNERS

(75) Inventors: Thomas Louis Toth, Brookfield, WI (US); Armin Horst Pfoh, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 1033 days.

(21) Appl. No.: 08/576,066

(22) Filed: Dec. 21, 1995

(51) Int. Cl.[7] .................................................. A61B 6/00
(52) U.S. Cl. ......................... 378/19; 378/207; 378/113
(58) Field of Search .............................. 378/19, 20, 113, 378/137, 138, 205, 207, 146, 147

(56) References Cited

U.S. PATENT DOCUMENTS 5,241,576 A * 8/1993 Lonn ............................ 378/19
5,469,429 A * 11/1995 Yamazaki et al. ............ 378/19
5,550,886 A * 8/1996 Dobbs et al. ................. 378/19

FOREIGN PATENT DOCUMENTS

JP          06038956      * 2/1994   .................. 378/19

* cited by examiner

Primary Examiner—David P. Porta
(74) Attorney, Agent, or Firm—Carl B. Horton, Esq.; Armstrong Teasdale LLP

(57) ABSTRACT

Focal spot position determination systems having a high sensitivity to focal spot movement for use in connection with multi-slice computed tomography imaging systems are described. In one embodiment, the determination system is configured for application in a two slice system. Signals from adjacent detector cells in separate rows are compared to determine focal spot position. More particularly, the signal intensity A of the signal output by a first detector cell and the signal intensity B of the signal output by the second detector cell are related to the position of the focal spot. That is, the z position of the centerline of the fan beam can be determined by relating the signal intensities A and B according to the ratio [(A−B)/(A+B)]. Such ratio is representative of the beam location and can be used to control adjustment of the imaging system pre-patient collimator to maintain the beam in the desired position.

16 Claims, 4 Drawing Sheets

METHODS AND SYSTEMS FOR DETERMINING X-RAY BEAM POSITION IN MULTI-SLICE COMPUTED TOMOGRAPHY SCANNERS

FIELD OF THE INVENTION

This invention relates generally to computed tomography (CT) imaging and more particularly, to determining x-ray beam position in a multi-slice CT system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

Known CT scanners include a pre-patient collimating device having an aperture that defines the x-ray beam profile in the z-axis (patient axis). When performing a scan, the x-ray beam typically moves up to 2 mm in the z-direction on tile detector array due to thermal, gravitational, and centrifugal force effects. This movement of the fan beam affects the signal strength at the detector, which results in artifacts in a reconstructed image.

Known CT scanners perform data corrections to compensate for detector signal variation as a function of z-axis x-ray beam position on the detector. More particularly, multi-slice CT systems typically utilize a precise closed loop z-axis tracking system to minimize beam motion and to perform z-axis corrections to compensate for z-axis beam motion and better utilize x-ray dosage. Known z-axis beam position sensing devices, or z-axis offset detectors, include a metal wedge or series of alternate wedges that are placed over one or more detector channels to induce a significant and repeatable signal variation as a function of the z-axis position. A detailed description of detecting fan beam positions by using known wedges is described, for example, in U.S. Pat. No. 4,559,639, entitled "X-Ray Detector with Compensation for Height-Dependant Sensitivity," assigned to the present assignee and incorporated herein by reference.

Although the known z-axis beam position sensing devices provide acceptable results, e.g., artifact reduction, it would be desirable to increase beam position measurement sensitivity and accuracy to further improve artifact reduction. It also would be desirable to improve artifact reduction without significantly increasing the system cost and processing time.

SUMMARY OF THE INVENTION

These and other objects may be attained in a system for determining x-ray beam position by utilizing signals from detector data or z position cells to generate difference, or ratio, signals representative of beam position. Such difference or ratio signals can then be used to control the pre-patient collimator so that if the beam is out of alignment, the beam is brought back into alignment by the collimator. The present invention is particularly applicable in multi-slice computed tomography systems, including two and four slice systems.

In a two slice system, for example, a collimated x-ray beam is projected toward two adjacent first and second detector cells. A plane, generally referred to as the "fan beam plane", contains the centerline of focal spot and the centerline of the beam. When the beam is positioned in its most desirable orientation, the fan beam plane is aligned with the centerline $D_o$ of the exposure area on the adjacent detector cells.

The signal intensity A of the signal output by the first detector cell and the signal intensity B of the signal output by the second detector cell are related to the position of the focal spot. Specifically, the z position of the centerline of the fan beam can be determined by relating the signal intensities A and B according to the ratio $[(A-B)/(A+B)]$. Such ratio is representative of the beam location and can be used to control adjustment of the collimator to maintain the beam in the desired position.

The above described system has a high sensitivity to focal spot movement and generates a signal accurately representative of focal spot position. Such high sensitivity and accuracy facilitates improving artifact reduction. Further, such improved artifact reduction can be achieved without significantly increasing the system cost and processing time.

DETAILED DESCRIPTION OF THE DRAWINGS

Figure 1:
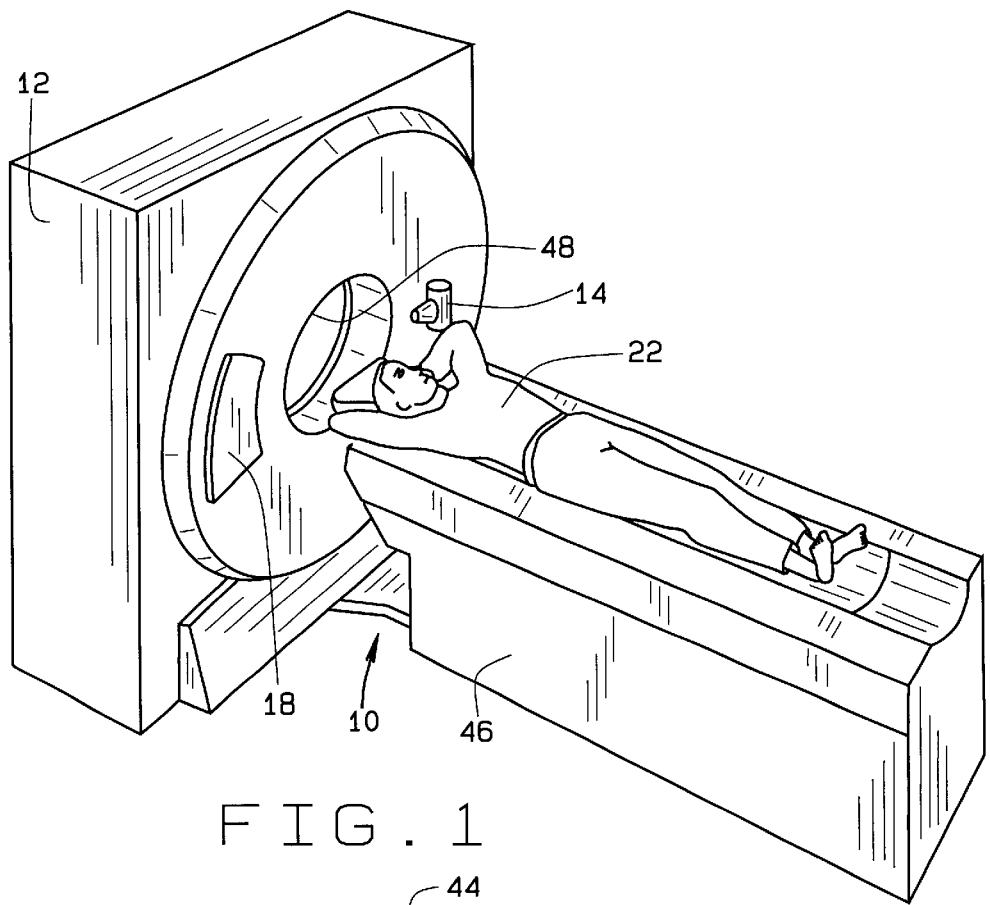
FIG. 1 is a pictorial view of a CT imaging system.
Figure 2:
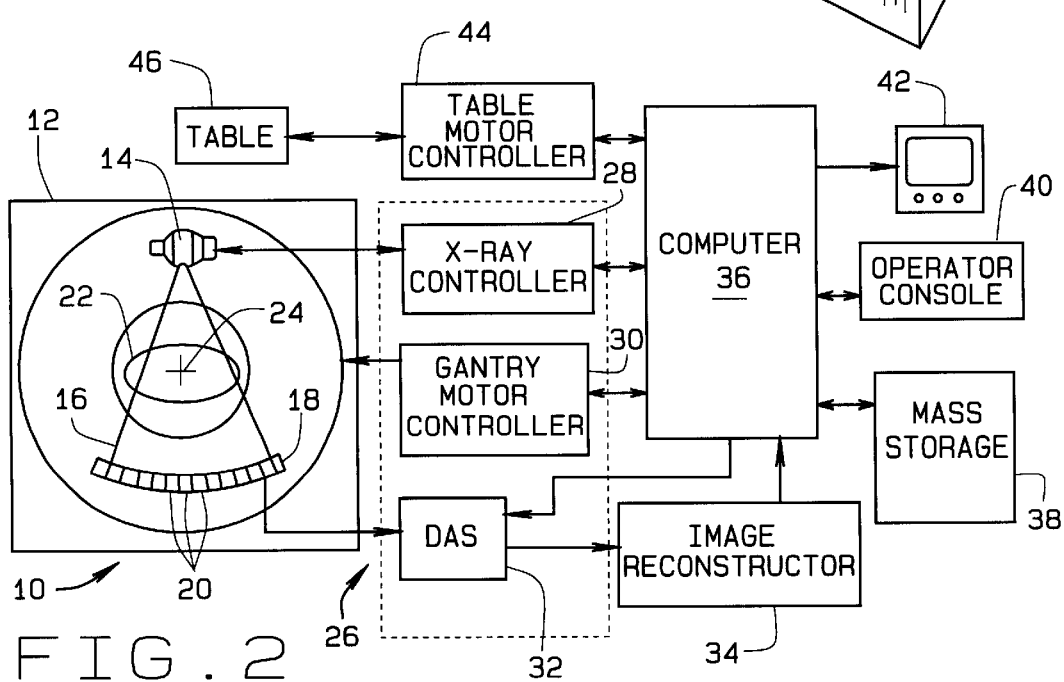
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24 within the x-y plane of a Cartesian Coordinate System.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
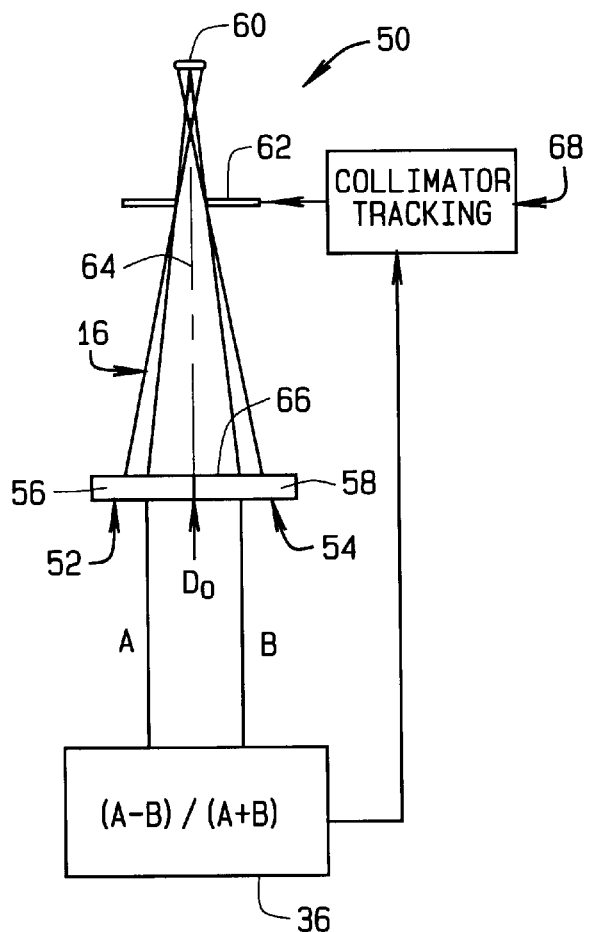
FIG. 3 is a schematic view of one embodiment of an x-ray beam position determination system in accordance with the present invention.

FIG. 3 is a schematic view of one embodiment of an x-ray beam position determination system 50 in accordance with the present invention. System 50 is a "two slice" system in that two rows 52 and 54 of detector cells are utilized to obtain projection data. Detector cells 56 and 58, in addition to obtaining projection data, are utilized for determining x-ray beam z-axis position.

More specifically, and as shown in FIG. 3, x-ray beam 16 emanates from a focal spot 60 of x-ray source 14 (FIG. 2). X-ray beam 16 is collimated by a pre-patient collimator 62, and collimated beam 16 is projected toward detector cells 56 and 58. A plane 64, generally referred to as the "fan beam plane", contains the centerline of focal spot 60 and the centerline of beam 16. In FIG. 3, fan beam plane 64 is aligned with the centerline $D_o$ of exposure area 66 on detector cells 56 and 58.

The signal intensity A of the signal output by detector cell 56 and the signal intensity B of the signal output by detector cell 58 are related to the position of focal spot 60. Specifically, the z position of centerline 64 of fan beam 16 can be determined by relating the signal intensities A and B according to the ratio [(A−B)/(A+B)]. Such ratio can be determined by computer 36 (FIG. 2). The measured z position signal may then be used to adjust the position of collimator 62 to correct the position of fan beam 16 in the z plane. The z position signal may be used to adjust the collimator position, for example, as described in U.S. Pat. No. 4,991,189 entitled "Collimation Apparatus for X-Ray Beam Correction," assigned to the present assignee and incorporated herein by reference in its entirety.

As one specific example, and if centerline 64 of beam 16 is centered on the centerline Do of exposure area 66, then signal A and B from cells 56 and 58 would be approximately equal. Therefore, A−B would approximately equal zero. The ratio [(A−B)/(A+B)] thus would equal zero. A value of about zero therefore would be provided by computer 36 to collimator tracking mechanism 68 and collimator 62 would not be adjusted.

As another example, if centerline 64 of beam 16 falls on the surface of detector cell 56, signal A would have a higher value than signal B. Ratio [(A−B)/(A+B)] therefore would be a positive value. Conversely, if centerline 64 of beam 16 falls on the surface of detector cell 58, signal B would have a higher value than signal A. Ratio [(A−B)/(A+B)] therefore would be a negative value.

By using the above described ratio, as opposed to a z-wedge detector, beam position measurement sensitivity and accuracy is improved so that artifact reduction can be further improved. Specifically, the signal to noise ratio, i.e., the signal change with respect to a given beam movement divided by quantum noise, for a 1 mm beam is believed to be 5 times better than with known z-offset detectors. Further, use of such a ratio is believed to improve artifact reduction without significantly increasing the system cost and processing time.

Figure 4A:
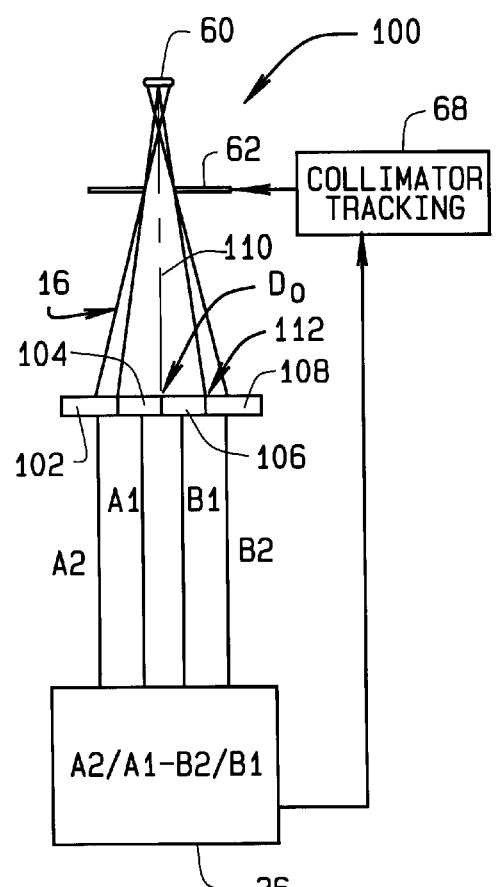
FIGS. 4a, 4b and 4c are schematic views of another embodiment of an x-ray beam position determination system in accordance with the present invention.

FIG. 4a is a simplified schematic view of another embodiment of an x-ray beam position determination system 100 in accordance with the present invention. Components in system 100 which are identical to components in system 50 (FIG. 3) are identified in FIGS. 4a, 4b and 4c using the same reference numerals as used in FIG. 3. System 100 is a "four (or quad) slice" system in that four rows 102, 104, 106 and 108 of detector cells are utilized to obtain projection data. Detector cells, sometimes referred to as z position cells, 102, 104, 106 and 108 are utilized for determining x-ray beam z-axis position.

Figure 4B:
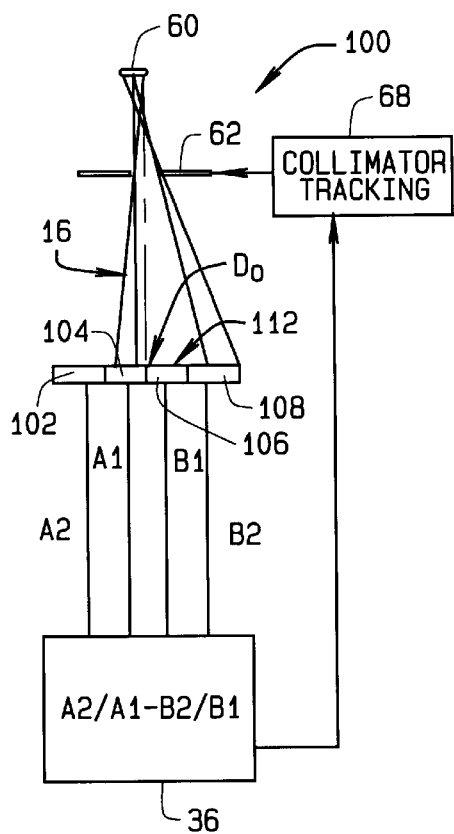
Figure 4C:
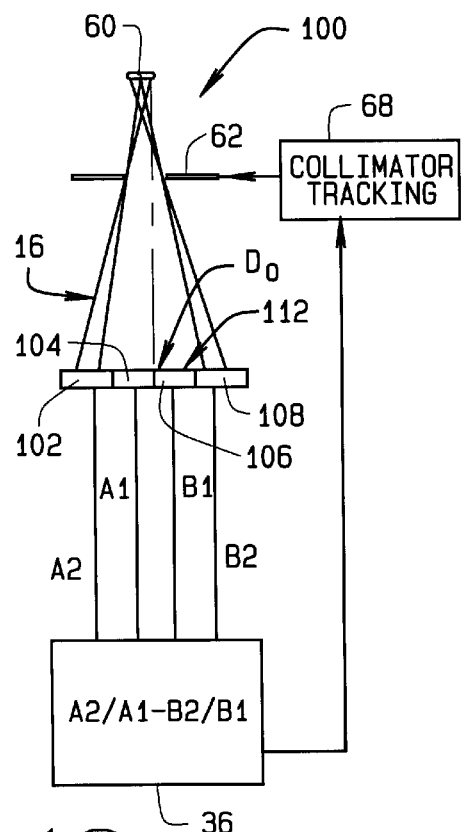

As in system 50 (FIG. 3), and referring to FIGS. 4a, 4b and 4c, x-ray beam 16 emanates from a focal spot 60 of x-ray source 14 (FIG. 2). X-ray beam 16 is collimated by a pre-patient collimator 62, and collimated beam 16 is projected toward detector cells 102, 104, 106, and 108. As shown in FIG. 4a, a plane 110, generally referred to as the "fan beam plane", contains the centerline of focal spot 60 and the centerline of beam 16.

In FIG. 4a, fan beam plane 110 is aligned with the centerline $D_o$ of exposure area 112 on detector cells 102, 104, 106 and 108. Opposing peripheral cells 102 and 108 generate signals having signal intensities A2 and B2, respectively. Similarly, opposing interior cells 104 and 106 generate signals having signal intensities A1 and B1, respectively. Cells 104 and 106 typically are located within the beam umbra and cells 102 and 108 typically receive both beam umbra and penumbra.

The signal intensities A1, A2, B1, B2 are related to the position of focal spot 60. Specifically, the z position of focal spot 60 can be determined by relating the signal intensities A1, A2, B1 and B2 according to the difference [(A2/A1)−(B2/B1)]. Such difference can be determined by computer 36 (FIG. 2).

As one specific example, and still referring to FIG. 4a, if centerline 110 of beam 16 is centered on the centerline $D_o$ of exposure area 112, then signals A2 and B2 from cells 102 and 108 would be approximately equal and signals A1 and B1 from cells 104 and 106 would be approximately equal. Therefore, the difference [(A2/A1)−(B2/B1)] would approximately equal zero. A value of about zero therefore would be provided by computer 36 to collimator tracking mechanism 68 and collimator 62 would not be adjusted.

As another example, and referring to FIG. 4b, if centerline 110 of beam 16 shifts so that a greater portion of beam 16 falls on the surface of cells 106 and 108 as shown, then signal intensity B2 would be greater than signal intensity A2. Also, if the shift is significant enough so that cell 104 is not flooded, then signal intensity B1 would be greater than signal intensity A1. Therefore, the difference [(A2/A1)−(B2/B1)] would be a negative value.

Referring to FIG. 4c, and if the difference [(A2/A1)−(B2/B1)] is negative, a negative value, for example, would be provided by computer 36 to collimator tracking mechanism 68 and collimator 62 would be adjusted to bring beam 16 into more desirable alignment. Therefore, as shown in FIG. 4c, even though focal spot 60 is not aligned with centerline $D_o$ of exposure area 112, beam 16 is substantially aligned with exposure area 112 so that center axis 110 of beam 16 is directed towards centerline $D_o$.

As yet another example, and although not shown, if centerline 110 of beam 16 shifts so that a greater portion of beam 16 falls on the surface of cells 102 and 104, then signal intensity A2 would be greater than signal intensity B2. Also, if the shift is significant enough so that cell 106 is not flooded, then signal intensity A1 would be greater than signal intensity B1. Therefore, the difference [(A2/A1)−(B2/B1)] would be a positive value. A negative value, for example, would be provided by computer 36 to collimator tracking mechanism 68 and collimator 62 would be adjusted to bring beam 16 into more desirable alignment.

Figure 5:
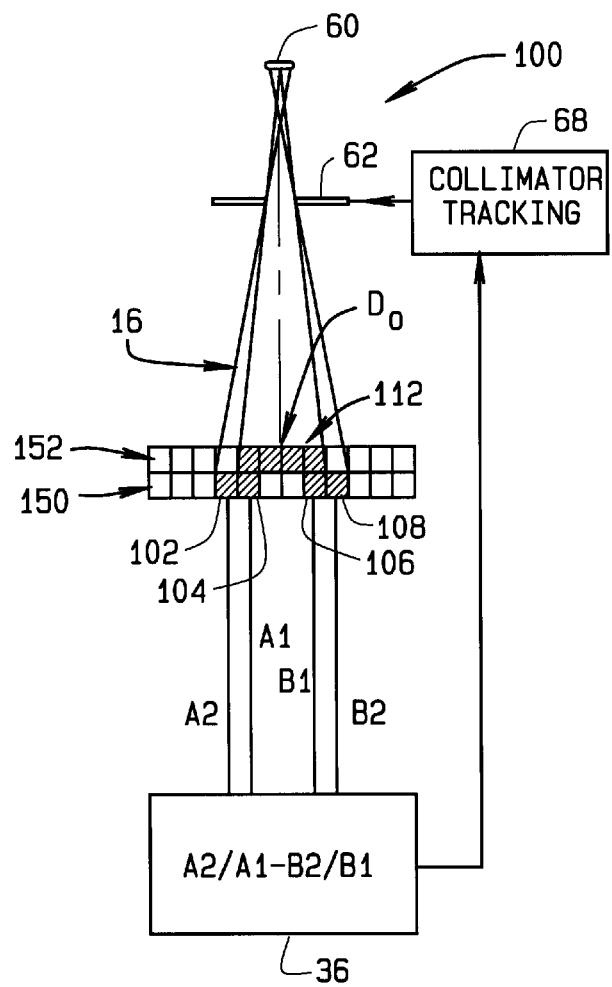
FIG. 5 is a more detailed schematic view of the x-ray beam position determination system shown in FIGS. 4a, 4b and 4c.

FIG. 5 is a more detailed schematic view of x-ray beam position determination system 100 shown in FIGS. 4a, 4b and 4c. Specifically, as shown in FIG. 5, detector (or data) cells 102, 104 106 and 108 are in a z-axis position (or z sensing) array 150. A second array 152 is used for collecting projection data. Of course, additional detector arrays may be used in system 100.

System 100 may be referred to as a differential penumbra detector system in that outer data cells 102 and 108 are selected to be in the penumbra of beam 16. Inner data cells 104 and 106 are selected to be in the umbra of beam 16. As explained above, the signal intensities A1, A2, B1, B2 are related to the position of focal spot 60. Specifically, the z position of focal spot 60 can be determined by relating the signal intensities A1, A2, B1 and B2 according to the difference [(A2/A1)−(B2/B1)]. Such difference can be determined by computer 36 (FIG. 2).

An additional advantage of system 100 is improved blocked signal performance. Particularly, position errors generated when sensing cells 102, 104, 106 and 108 are blocked by patient anatomy are reduced since the blocking anatomy is similar for the penumbra cells 102 and 108 and for the umbra cells 104 and 106. Therefore, there is less relative signal error.

Figure 6:
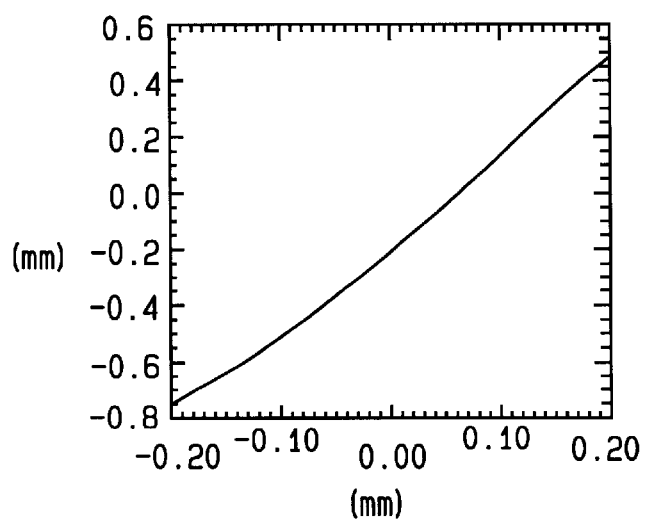
FIG. 6 is a graph illustrating differential signal versus focal spot z position.

FIG. 6 is a graph illustrating differential signal versus focal spot z position. The graph was generated to simulate detector cell response for system 100. As shown in the graph, the curve slope is steep so that any misalignment of focal spot, in millimeters, results in a significant change in the difference [(A2/A1)−(B2/B1)]. Such high sensitivity and accuracy facilitates improving artifact reduction. Further, such improved artifact reduction can be achieved without significantly increasing the system cost and processing time.

Of course, to provide a more consistent focal spot position versus differential signal response, the outputs of cells 102, 104, 106 and 108 may be calibrated. For example, signal A1 could be set to equal $(g_{a1} \times a1)$ where $g_{a1}$ is the gain correction factor of cell 104 and a1 equals the raw signal output by cell 104. Similarly, B1 could be set to equal $(g_{b1} \times b1)$ where $g_{a1}$ is the gain correction factor for cell 106 and b1 equals the raw signal output by cell 106. When both cells 104 and 106 are fully flooded by beam umbra, then gain correction factors $g_{a1}$ and $g_{b1}$ could be selected so that A1=B1.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while the systems described herein have been two-slice, four-slice and six-slice, any multi-slice system may be used. Moreover, while the collimator tracking system has been described in detail, any known collimator tracking system may be used. Furthermore, any focal spot repositioning system or any detector repositioning system may be used. Accordingly, the spirit and scope of the invention are to be limited only by the terms of the appended claims.

What is claimed is:

1. A system for determining and adjusting x-ray beam position in a multi-slice computed tomography system, the computed tomography system including an x-ray source having a focal spot and a multi-slice detector having at least two rows of detector cells displaced along a z-axis, the x-ray source producing an x-ray beam along the z-axis, said beam position determining and adjusting system comprising an adjustable prepatient collimator aligned with the x-ray source so that a beam from the x-ray source is directed towards said collimator, a collimator tracking unit coupled to said collimator for adjusting the position of said collimator, and a control computer coupled to the detector cells for receiving signals from the cells, said control computer coupled to said collimator tracking unit for providing control signals thereto, said control computer configured to:

obtain separate signals from a first detector cell in the first detector cell row and a second detector cell in the second detector cell row of the detector;

determine beam position from the intensities of the separate signals; and provide control signals to said collimator tracking unit to control adjustment of said prepatient collimator based on a determined beam position.

2. A system in accordance with claim 1 wherein the signal from the first detector has an intensity A and the signal from the second detector has an intensity B, and determining beam position from the intensities A and B is performed using the relationship [(A−B)/(A+B)].

3. A system in accordance with claim 2 wherein the computed tomograph system is a two slice system.

4. A system in accordance with claim 1 wherein the computed tomography system has at least four rows of detector cells displaced along a z-axis, and wherein said beam position determining system is configured to:

obtain separate signals from a first detector in the first row, a second detector in the second row, a third detector in the third row, and a fourth detector in the fourth row; and determine beam position from the intensities of the separate signals.

5. A system in accordance with claim 4 wherein the signal from the first detector has an intensity A1, the signal from the second detector has an intensity A2, the signal from the third detector has an intensity B1, and the signal from the fourth detector has an intensity B2.

6. A system in accordance with claim 5 wherein a portion of the first detector is adjacent a portion of the third detector, and the first and third detectors are positioned to be substantially within an umbra of the x-ray beam.

7. A system in accordance with claim 6 wherein a portion of the second detector is adjacent a portion the first detector, and a portion of the fourth detector is adjacent a portion of the third detector, and the second and fourth detectors are positioned to be substantially within a penumbra of the x-ray beam.

8. A system in accordance with claim 7 wherein determining beam position from the intensities A1, A2, B1 and B2 is performed using the relationship $[(A2/A1)-(B2/B1)]$.

9. A method for determining and adjusting x-ray beam position in a multi-slice computed tomography system, the computed tomography system including an x-ray source having a focal spot and a multi-slice detector having at least two rows of detector cells displaced along a z-axis, the x-ray source producing an x-ray beam along the z-axis, the computed tomography system further including an adjustable prepatient collimator aligned with the x-ray source so that a beam from the x-ray source is directed towards the collimator, a collimator tracking unit coupled to the collimator for adjusting the position of the collimator, and a control computer coupled to the detector cells for receiving signals from the cells, the control computer coupled to the collimator tracking unit, said method comprising the steps of:

obtaining separate signals from a first detector cell in the first detector cell row and a second detector cell in the second detector cell row of the detector;

determining beam position from the intensities of the separate signals; and adjusting the prepatient collimator based on the determined beam position.

10. A method in accordance with claim 9 wherein the signal from the first detector has an intensity A and the signal from the second detector has an intensity B, and determining beam position from the intensities A and B is performed using the relationship $[(A-B)/(A+B)]$.

11. A method in accordance with claim 10 wherein the computed tomograph system is a two slice system.

12. A method in accordance with claim 9 wherein the computed tomography system has at least four rows of detector cells displaced along a z-axis, and wherein said method comprises the steps of:

obtaining separate signals from a first detector in the first row, a second detector in the second row, a third detector in the third row, and a fourth detector in the fourth row; and determining beam position from the intensities of the separate signals.

13. A method in accordance with claim 12 wherein the signal from the first detector has an intensity A1, the signal from the second detector has an intensity A2, the signal from the third detector has an intensity B1, and the signal from the fourth detector has an intensity B2.

14. A method in accordance with claim 13 wherein a portion of the first detector is adjacent a portion of the third detector, and the first and third detectors are positioned to be substantially within an umbra of the x-ray beam.

15. A method in accordance with claim 14 wherein a portion of the second detector is adjacent a portion the first detector, and a portion of the fourth detector is adjacent a portion of the third detector, and the second and fourth detectors are positioned to be substantially within a penumbra of the x-ray beam.

16. A method in accordance with claim 15 wherein determining beam position from the intensities A1, A2, B1 and B2 is performed using the relationship $[(A2/A1)-(B2/B1)]$.

* * * * *